United States Patent [19]

Nishida et al.

[11] Patent Number: Plant 6,540

[45] Date of Patent: Jan. 17, 1989

[54] PEACH TREE 'CHIYOHIMI'

[75] Inventors: Teruo Nishida, Tokyo; Masao Yoshida, Ibaraki; Hidetoshi Kyotani, Tokyo; Masami Yamaguchi; Teruo Kozono, both of Ibaraki, all of Japan

[73] Assignee: Fruit Tree Research Station, Ministry of Agriculture, Forestry and Fisheries, Tsukuba, Japan

[21] Appl. No.: 25,707

[22] Filed: Mar. 13, 1987

[30] Foreign Application Priority Data

Mar. 31, 1986 [JP] Japan ..... 61-1893

[51] Int. Cl.[4] ..... A01H 5/00

[52] U.S. Cl. ..... Plt./42

[58] Field of Search ..... Plt./42

[56] References Cited

PUBLICATIONS

Official Gazette No. 17792 (Jun. 6, 1986), pp. 12–13 (Japanese).

*Primary Examiner*—James R. Feyrer

*Attorney, Agent, or Firm*—Armstrong, Nikaido, Marmelstein & Kubovcik

[57] ABSTRACT

Disclosed herein is a peach tree of an early ripening cultivar which is self-fertile and productive with a low physiological fruit drop. The tree has showy and pink flowers with abundant pollen, and can produce a round elliptic, clingstone fruit with a good keeping quality, suitable for dessert. The fruit has a sturdy and attractive skin with a white ground color and a bright red blush, a melting flesh having a white color with some red pigment, a moderate firmness, moderate sweetness and a low acidity, giving a good taste.

4 Drawing Sheets

BACKGROUND OF THE VARIETY

The present invention relates to a new and distinct variety of peach tree having fruit which matures early in the season, and is self-fertile and productive with a low physiological fruit drop. The tree has showy and pink flowers with abundant pollen, and can produce a round elliptic, clingstone fruit suitable for dessert and with a good keeping quality. The fruit has a sturdy and attractive skin with a white ground color and a bright red blush, a melting flesh having a white color with some red pigment, a moderate firmness, moderate sweetness, and a low acidity, giving a good taste.

All places and addresses mentioned in this specification are in Japan, unless otherwise specified.

Our breeding program was aimed at obtaining a new variety of peach tree producing, first, a fruit having a high marketability for dessert due to a good appearance, taste, texture and keeping quality, and maturing early in the season; second, bearing stably and resistant to pests and diseases; and third, easy to grow and possible to grow without bagging.

The new variety of peach tree according to this invention originated from crossing 'Kōyōhakutō (♀)'×'Saotome (♂)' in 1973 at the Fruit Tree Research Station, Ministry of Agriculture, Forestry and Fisheries, residing at Ōhara, Hiratsuka-shi, Kanagawa-ken, Japan. The seedling was planted and numbered as '65-13' in 1974 at the Chiyoda Experiment Farm of the Fruit Tree Research Station, Ministry of Agriculture, Forestry and Fisheries, residing at Kamishizuku, Chiyoda-mura, Niihari-gun, Ibaraki-ken, Japan. The tree bore fruit for the first time in 1976. The tree was selected, first, with regard to the quality of the fruit and the growing character, in 1978. From 1981, the thus-selected tree was subjected to local adaptability tests at the experimental stations in Fukushima-ken, Yamanishi-ken, Okayama-ken and the like, as the number 'Peach Tsukuba—84'. As a result, this new variety of peach tree according to this invention was judged to have a good quality fruit and growing character. This new variety of peach tree was named 'Chiyohime', in June 1986.

The pedigree of 'Chiyohime' is shown in FIG. 1.

It is known that 'Kōyōhakutō', used as a female parent in the breeding of 'Chiyohime', was discovered as a bud-mutant among the 'Hakutō' trees planted at Kōyō-mura, Akaiwa-gun, Okayama-ken, Japan. 'Kōyōhakutō' attracted general attention from about 1950. The main botanical characteristics of 'Kōyōhakutō' suitable for dessert are as follows.

Tree:
- *Habit of branches.*—Spreading.
- *Vigor.*—Strong.
- *Flower bud.*—Many.
- *Thickness of shoot.*—Thick.

Leaves:
- *Size.*—Medium.
- *Color.*—Green.
- *Glands.*—Reniform.

Flowers: Male — sterile.
- *Form.*—Showy.
- *Color.*—Pink.
- *Flowering time.*—Late, e.g., early-to-mid April in Okayama-ken, Japan.

Fruit:
- *Size.*—Large, 200–250 g.
- *Shape.*—Round elliptic.
- *Color of skin.*—White with attractive red blush.
- *Color of flesh.*—White with red around stone.
- *Flesh.*—Melting, firm (same as 'Hakutō'), with a fine texture and juicy when fully-ripe.
- *Taste.*—Sweet.
- *Ripening time.*—Mid — late season, e.g., early-to-mid August in Okayama-ken, Japan.
- *Keeping quality.*—Good.
- *Shipping quality.*—Good.

Culture: The tree is suitable for growth in fertile soil. Artificial pollination must be carried out, as the flowers have no pollen.

'Saotome', used as a male parent in the breeding of 'Chiyohime', originated from a crossing of 'Hakuhō'×'Robin' in 1957 at the Horticulture Division of National Institute of Agriculture, of the Ministry of Agriculture and Forestry, residing at Nakaharashimojuku, Hiratsuka-shi, Kanagawa-ken, Japan, was selected from the seedlings as the individual number 'Se-13' in 1964, and thereafter, from 1972, was subjected to local adaptability tests at many experimental stations in peach growing districts of Japan. As a result, the tree was judged to be good, and was named 'Saotome', in October, 1982. The main botanical characteristics of 'Saotome' suitable for dessert are as follows.

Tree:
- *Habit of branches.*—Slightly upright.
- *Vigor.*—Strong.
- *Production.*—Productive.

Leaves:
- *Size.*—Large.
- *Shape.*—Lanceolate.
- *Color.*—Green.
- *Glands.*—Reniform.

Flowers: Self-fertile.
- *Form.*—Showy.
- *Color.*—Pink.
- *Pollen.*—Abundant.
- *Flowering time.*—Middle, e.g., early April in Kanagawa-ken, Japan.

Fruit:
- *Size.*—Small, 80–120 g.
- *Shape.*—Round to oblate and uniform.
- *Color of skin.*—White ground color with bright red blush.
- *Color of flesh.*—White with no red pigment.
- *Flesh.*—Soft melting, fine texture, and juicy.
- *Stone.*—Clingstone with some pit splitting.
- *Taste.*—Moderately sweet (about 10 in refractometer index) and low acid (about pH 4.3–4.5).
- *Ripening time.*—Very early (ripening in early June in Shizuoka-ken, mid-June in southwestern regions of Japan, late June in Okayama-ken and Yamanashi-ken, and early July in Fukushima-ken, Japan). An average of 73 days will elapse between full bloom and ripening.

Culture: The fruit ripens very early and thus suffer little damage by pests and diseases, and are easy to grow without bagging.

We asexually reproduced this new and distinct variety of peach tree 'Chiyohime', by grafting at the Chiyoda Experiment Farm of the Fruit Tree Research Station, Ministry of Agriculture, Forestry and Fisheries, and confirmed the homogeneity and stability of 'Chiyohime' according to this invention.

An application for this new variety of peach tree 'Chiyohime' under the Seeds and Seedlings Law of Japan was filed on Mar. 31, 1986.

SUMMARY OF THE VARIETY

The new variety of peach tree has a medium vigor, is self-fertile with abundant pollen, has a good bearing character, is productive with a low physiological fruit drop, and has pink, showy and large flowers. The tree produces a clingstone fruit having a good keeping quality, a round elliptic shape, and a sturdy and attractive skin having a white ground color with a bright red blush. The fruit matures early in the season, a few days later than 'Saotome' and a few days earlier than 'Nunomewase' (i.e., typical Japanese commercial early variety of peach with a white flesh). The fruit has a melting flesh having a white color with some red pigment and a moderate firmness. The flesh is fine and juicy, has a moderate sweetness and low acidity, and has a good taste for dessert.

DESCRIPTION OF THE VARIETY

The botanical characteristics of the new and distinct variety of peach tree 'Chiyohime' are as follows.

Figure 2:
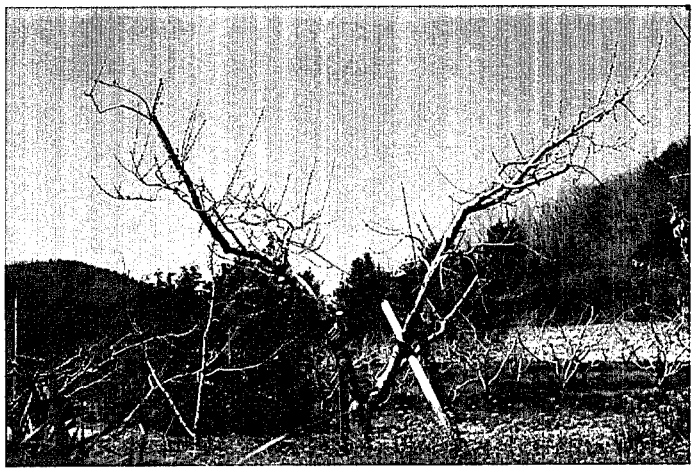
FIG. 2 is a photograph of a shape of the new variety of peach tree.

Tree: Having a good bearing character.
- *Habit of branches.*—Moderate spreading (See FIG. 2).
- *Size.*—Medium.
- *Vigor.*—Medium, same as 'Kōyōhakutō' but weaker than 'Saotome'.
- *Production.*—Productive.

Trunk:
- *Size.*—Medium.

Branches:
- *Size.*—Medium.

Figure 3:
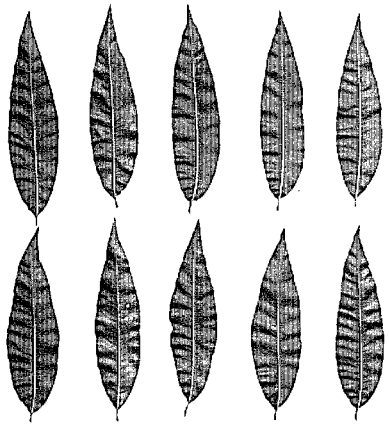
FIG. 3 is a photograph of leaves of the new variety of peach tree.

Leaves:
- *Size.*—Medium.
- *Shape.*—Lanceolate.
- *Color.*—Green.
- *Glands.*—Reniform. (See FIG. 3).

Figure 4:
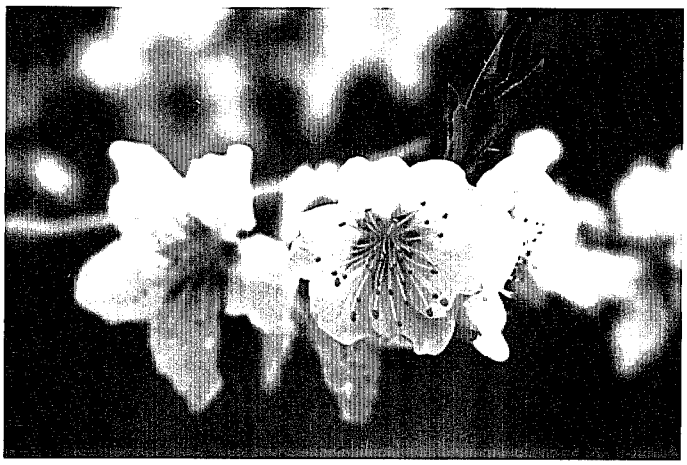
FIG. 4 is a photograph of flowers of the new variety of peach tree.
Figure 5:
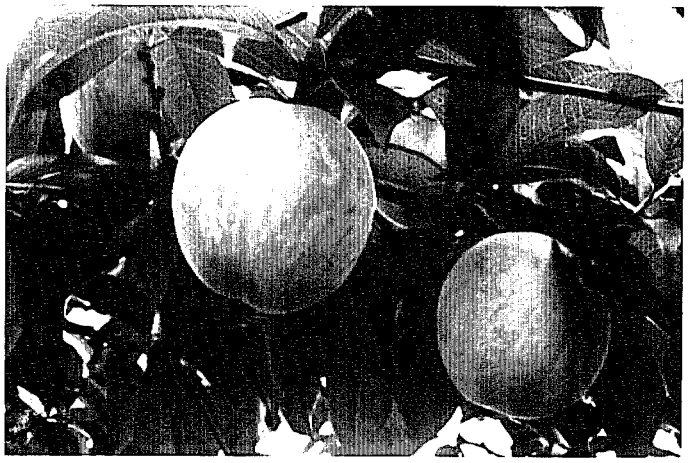
FIG. 5 is a photograph of the new variety of peach tree when bearing fruit; and, FIG. 6 is a photograph giving top, cross-sectional and side views of fruit, from the left, of the new variety of peach tree.
Figure 6:
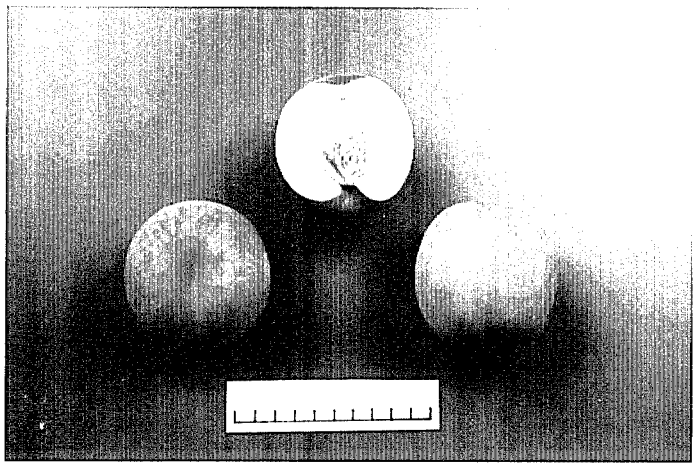

Flowers: Self-fertile.
- *Form.*—Showy.
- *Size.*—Large.
- *Color.*—Pink. (See FIG. 4).
- *Flower bud.*—Many.
- *Pollen.*—Abundant.
- *Flowering time.*—Middle, almost same season as 'Saotome' and 'Nunomewase' and a little earlier than 'Hakuhō' (e.g., early April in Kanagawa-ken, and mid-April in Ibaraki-ken, Japan).
- *Physiological fruit drop.*—Low.

Fruit:
- *Size.*—Small to medium, 120–180 g, averaging 150 g, larger than 'Saotome', and slightly smaller than 'Nunomewase'.
- *Shape.*—Round elliptic with cavity having medium depth and width, and clear suture.
- *Color of skin.*—Attractive, white ground color with bright red blush coloring, the degree of coloring being similar to 'Saotome' and higher than 'Nunomewase'.

*Skin.*—Slightly thick, but thinner than 'Kōyōhakutō'. Sturdy.

*Color of flesh.*—White with some red pigment.

*Flesh.*—Melting, having a moderate firmness but softer than 'Kōyōhakutō', medium fiber amount, juicy, and having a fine texture.

*Stone.*—Medium size clingstone.

*Taste.*—Good, with moderate sweetness of about 10 in refractometer index, 1 point higher than 'Nunomewase' in the same index, a low acidity of a pH of 4.2–4.6, averaging 4.5, and little astringency.

*Maturity.*—Maturing early in the season and taking 77 days from full bloom to ripening, which is a little more than 'Saotome' (73 days) and a little less than 'Nunomewase' (80 days). The maturing time is early-to-mid June in southwestern warm climate regions in Japan, e.g., Kagoshima-ken and Kōchi-ken, mid-to-late June in Tōkai districts of Japan, late June in Okayama-ken and Yamanashi-ken, early-to-mid July in Fukushima-ken, and mid-July in Yamagata-ken, Japan.

*Use.*—Suitable for dessert.

*Keeping quality.*—Good. Can be kept for 5 to 7 days, which is better than 'Nunomewase'.

*Shipping quality.*—Good due to sturdy skin having a medium firmness.

Resistance to pests and diseases: Above average.

Chilling requirement: The tree is suitable for a temperate zone.

Culture: The tree is easy to manage due to its moderate vigor. It is necessary to ensure that the fruit bearing is not too heavy, as the tree is self-fertile and bears well. Careful attention must be paid to the degree of maturity and the fruit must not be picked early. This is because, although the skin tends to have a red coloring, the fruit has an unpreferably hard textured flesh and a poor taste. A medium size fruit should be produced, since large size fruit has more possibility of pit-splitting. Cultivation without bagging is both possible and desirable, as the fruit ripens early and sustains little damage by pests and diseases. The tree is easy to grow, because it has a low physiological fruit drop and bears stably.

The tree of this new variety 'Chiyohime' is presently planted and maintained at the Chiyoda Experimental Farm of the Fruit Tree Research Station, Ministry of Agriculture, Forestry and Fisheries, residing at 418-1 Kamishizuku, Chiyoda-mura, Niihari-gun, Ibaraki-ken, Japan.

We claim:

1. A new and distinct variety of peach tree, substantially as illustrated and described herein, characterized over known peach trees by (A) having a moderate vigor, (B) being self-fertile with abundant pollen, (C) having a good bearing character and being productive with a low physiological fruit drop, (D) having pink, showy and large flowers, and (E) producing a clingstone fruit (a) having a good keeping quality, a round elliptic shape and sturdy and attractive skin having a white ground color with a bright red blush, (b) maturing early in the season, a few days later than 'Saotome' and a few days earlier than 'Nunomewase', and (c) having a melting flesh having a white color with some red pigment, which has a moderate firmness, is fine and juicy, has a moderate sweetness and a low acidity, and has a good taste for dessert.

* * * * *

Figure 1:
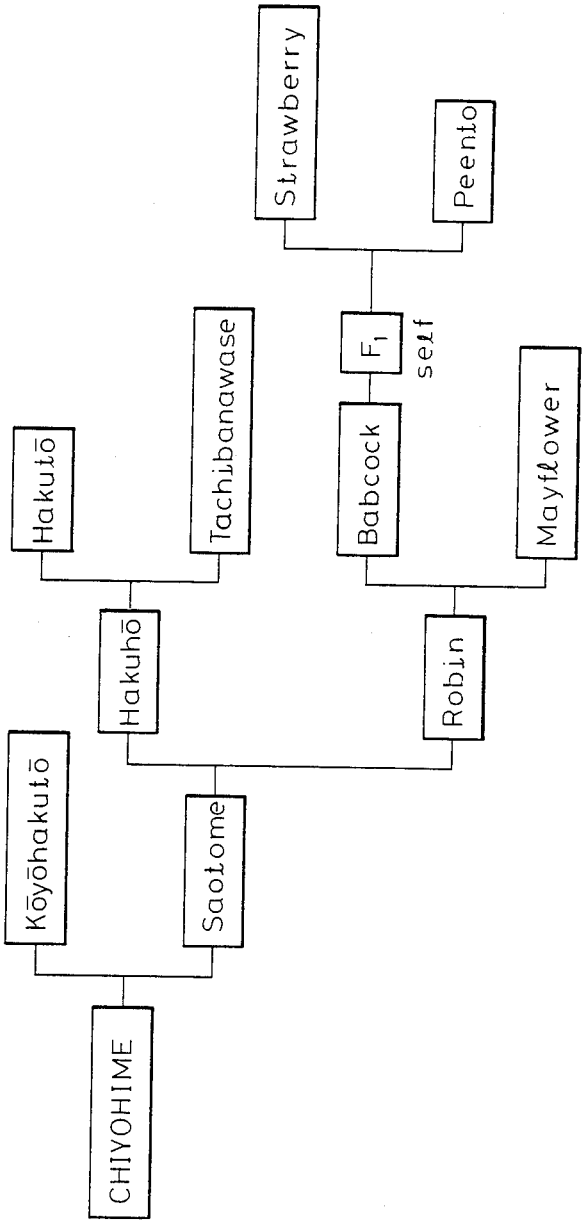
FIG. 1 gives the pedigree of the new and distinct variety of peach tree 'Chiyohime'.

Fig. 1 Pedigree of 'CHIYOHIME'

UNITED STATES PATENT AND TRADEMARK OFFICE

CERTIFICATE OF CORRECTION

PATENT NO. : Plant 6,540

DATED : January 17, 1989

INVENTOR(S) : Teruo NISHIDA et al

It is certified that error appears in the above-identified patent and that said Letters Patent is hereby corrected as shown below:

On the cover page, Item [54], " 'CHIYOHIMI' " should read -- 'CHIYOHIME' --.

Signed and Sealed this

Eighth Day of August, 1989

*Attest:*

*Attesting Officer*

DONALD J. QUIGG

*Commissioner of Patents and Trademarks*